United States Patent [19]
Itoigawa et al.

[11] Patent Number: 5,807,265
[45] Date of Patent: Sep. 15, 1998

[54] CATHETER HAVING PRESSURE DETECTING ABILITY

[75] Inventors: Koichi Itoigawa; Hitoshi Iwata, both of Aichi-ken, Japan

[73] Assignee: Kabushiki Kaisha Tokai Rika Denki Seisakusho, Aichi, Japan

[21] Appl. No.: 777,900

[22] Filed: Dec. 30, 1996

[30] Foreign Application Priority Data

Jan. 9, 1996 [JP] Japan ................................ 8-001800

[51] Int. Cl.⁶ ........................... A61K 9/00; A61M 5/00
[52] U.S. Cl. ........................................ 600/486; 424/400
[58] Field of Search ........................ 604/264; 424/400, 424/422, 423; 600/486

[56] References Cited

U.S. PATENT DOCUMENTS

| | | | |
|---|---|---|---|
| 4,329,994 | 5/1982 | Cooper | 128/349 B |
| 4,809,709 | 3/1989 | Brooks | 128/748 |
| 5,050,297 | 9/1991 | Metzger | 29/855 |
| 5,133,358 | 7/1992 | Gustafson et al. | 128/675 |

*Primary Examiner*—Thurman K. Page
*Assistant Examiner*—Kathryne E. Shelborne
*Attorney, Agent, or Firm*—Seth M. Reiss

[57] ABSTRACT

A catheter having a sensor for detecting forces acting on its distal end includes a catheter tube, a chamber defined in the catheter tube. The chamber is filled with silicon gel. The catheter also has a sensor chip and a cap. The sensor has a pressure sensing surface and a backside. The cap transmits the forces acting on the distal end of the catheter tube to the pressure sensing surface of the sensor chip. Further, the catheter has a pressure introducing hole. The pressure introducing hole transmits the forces acting on the periphery of the catheter tube to the backside of the sensor chip. The sensor chip issues signals externally in accordance with the pressures transmitted to its pressure sensing surface and its backside.

17 Claims, 5 Drawing Sheets

Fig.7 (従来技術)
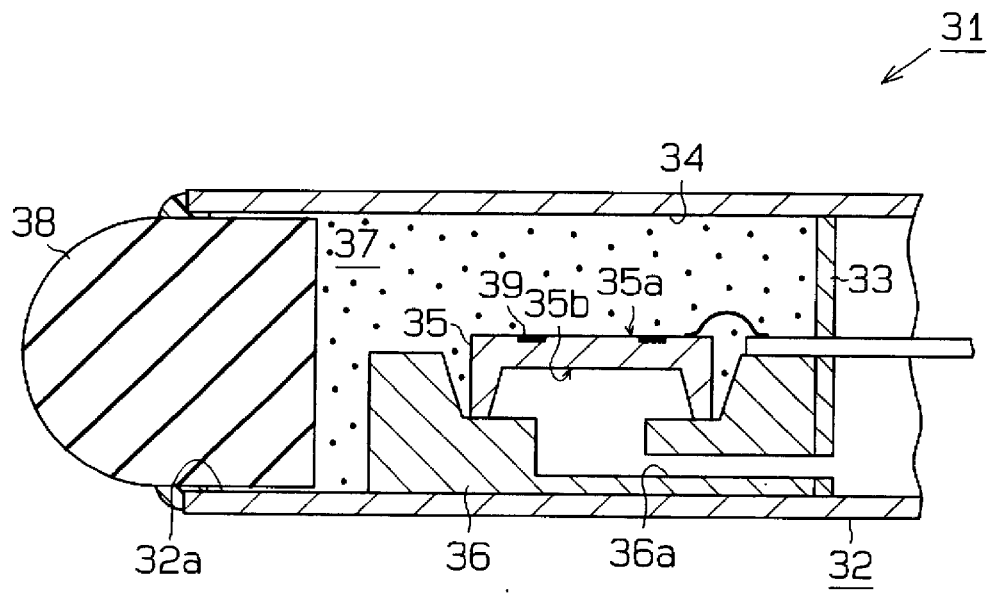
Fig.8 (従来技術)
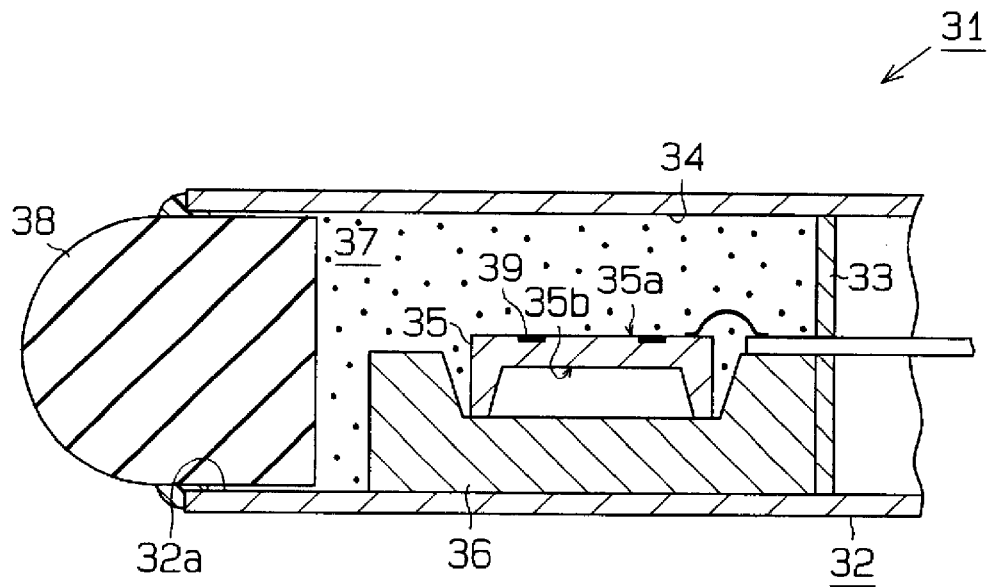

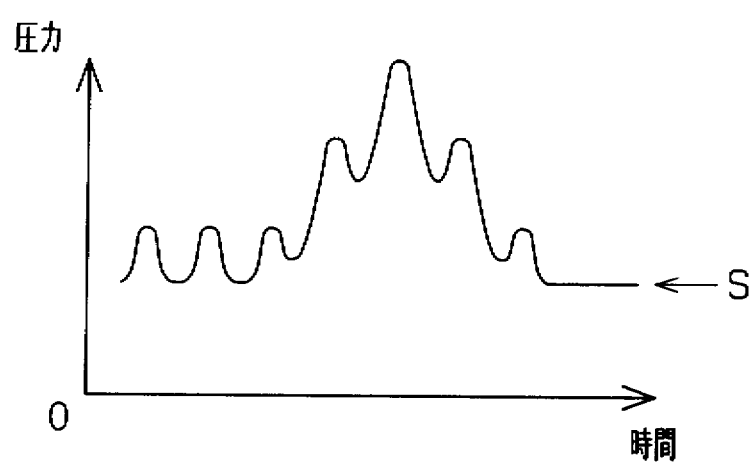
Fig.9 (従来技術)

CATHETER HAVING PRESSURE DETECTING ABILITY

BACKGROUND OF THE INVENTION

1. Field of the Invention

The present invention relates to a catheter, and more particularly, to a catheter that detects forces applied to the distal end of the catheter when inserted into the human body.

2. Description of the Related Art

Catheters are a type of medical instrument insertable into the human body. Catheter tubes, which constitute catheters, have diameters of approximately 1 mm to 9 mm and are inserted into various vessels within the human body, one being a blood vessel. The distal end of the catheter tube is guided into a desired position of the body to carry out medical treatments such as measurements of blood pressure and expansion of blood vessels at this position. Thus, the operator of the catheter must accurately guide the distal end of the catheter tube to the desired position by means of external operations.

The vessels within the human body often bend and branch off in different directions and are not necessarily straight. Furthermore, the diameter of the vessels are not always uniform but are naturally very small or have become small due to obstructions including blood clots existing within the vessels.

However, with a conventional catheter that is not provided with a means to detect the forward travel direction of the catheter tube, the operator must rely on his own feeling to operate the catheter tube. Hence, skill is necessary to guide the distal end of the catheter tube to the desired position.

In order to eliminate this problem, it has recently been proposed to provide sensors on the distal end of the catheter tube for detecting obstructions and operating the catheter tube based on the sensing result.

FIGS. 7 and 8 show a catheter 31 having the above described sensor 31.

A chip retaining chamber 34 is partitioned by a wall 33 in the distal portion of a catheter tube 32. A semiconductor pressure sensor chip 35 equipped with a distortion gauges 39 is stored within the chip retaining chamber 34 and is mounted to a substrate 36. Moreover, a silicon gel 37, which functions as a pressure transmitting medium, fills the inside of the chip retaining chamber 34. An opening 32a of the catheter tube 32 is sealed by an elastic cap 38.

Therefore, if forces are applied to the outer surface of the cap 38, they are transferred to the sensor chip 35 through the silicon gel 37 generating a variation in the electrical resistance value of the sensor chip 35. As a result, the sensor chip 35 outputs a signal S externally in response to the variations of the gel pressure (refer to FIG. 9). By monitoring the fluctuations of this signal S, the operator may sense the presence of an obstruction.

The sensor of FIG. 7 is of an atmospheric and relative pressure type, and the sensor of FIG. 8 is of an absolute pressure type. The sensor of FIG. 7 has a through hole 36a formed in the substrate 36. The back pressure, that is, the atmospheric pressure, acts on the backside 35b of the sensor chip 35 through the through hole 36a as a reference pressure. The sensor of FIG. 8 has no through hole 36a in the substrate 36. A vacuum chamber is provided adjacent to the back side 35b of the sensor chip 35.

However, when the catheter 31, which has the above structure, is inserted into a blood vessel, the following problems occur. Blood is always circulating through the blood vessels and the pressure of the blood fluctuates as time elapses. Consequently, components of the output signal S not only include fluctuation caused by contact with obstructions but also include fluctuation caused by blood pressure. The fluctuation caused by blood pressure appears regularly as a small pulse in the graph of FIG. 9. Therefore, with the catheter 31 having such structure, accurate sensing of the existence of an obstruction may be hindered, depending on the situation. There is thus a demand for a sensor that extracts the necessary signals from the output signals S.

SUMMARY OF THE INVENTION

The present invention addresses the above-mentioned problems. The objective of the present invention is to provide a catheter provided with a sensor that is capable of accurately sensing the state of the forward travel direction.

Another objective of the present invention is to provide a high quality sensor that is compact and easy to manufacture.

Yet another objective of the present invention is to provide a high quality sensor that is highly biocompatible.

BRIEF DESCRIPTION OF THE DRAWINGS

The features of the present invention that are believed to be novel are set forth with particularity in the appended claims. The invention, together with objects and advantages thereof, may best be understood by reference to the following description of the presently preferred embodiments together with the accompanying drawings in which:

FIG. 7 is a schematic cross-sectional view showing the distal portion of a catheter provided with a prior art sensor;

FIG. 8 is a schematic cross-sectional view showing the distal portion of a catheter provided with a prior art sensor; and FIG. 9 is a graph showing the waveform of output signals of a prior art sensor.

DETAILED DESCRIPTION OF THE PREFERRED EMBODIMENTS

Figure 1:
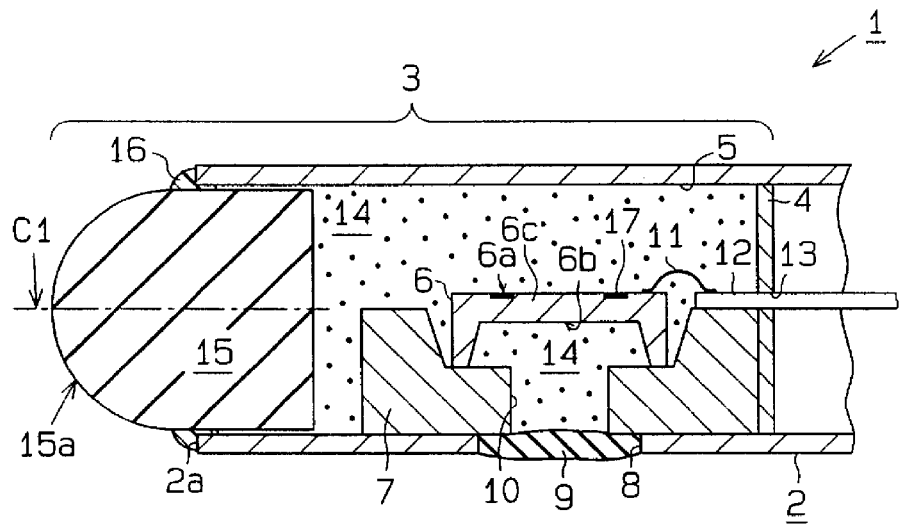
FIG. 1 is a schematic cross-sectional view showing a distal portion of a catheter provided with a sensor according to a first embodiment of the present invention.

A blood vessel catheter 1 according to a first embodiment of the present invention will now be described with reference to FIGS. 1 and 2.

The blood vessel catheter 1 is provided with a catheter tube 2 inserted into a blood vessel and a control device (not shown) located at a basal end of the tube 2 to operate the catheter tube 2 externally. The catheter tube 2 constitutes a portion of a catheter and is a flexible tube-shaped member that is inserted into the human body.

The control device is provided with, for example, a plurality of wires inserted inside the tube 2 and a wire control portion to control the wires. Further, an air compressor (not shown in figure) is arranged at the basal end of the tube 2 to inflate an expansion balloon provided near the distal end of the tube 2. An air supplying tube (not shown) is connected to the compressor. The air supplying pipe is inserted through the tube 2 and the distal end of the pipe is connected to the balloon. Air is supplied to expand the balloon and expand the constricted blood vessel from the inner side.

A sensor portion 3 is defined at the distal end of the catheter tube 2 in the catheter 1 of this embodiment. An opening 2a in the distal end of the catheter tube 2 is sealed by a cap 15 and a seal 16, which function as a sealing member. The seal 16 is elastic and ring-shaped. In addition to sealing the gap between the cap 15 and the opening 2a, the seal allows fine sliding movement along the axis C1 by the cap 15 relative to the tube 2.

A partition 4 is provided in the distal end of the tube 2. The cap 15 and the partition 4 define a chip retaining chamber 5 for the sensor portion 3. A semiconductor pressure sensor chip 6 is retained within the chip retaining chamber 5 mounted to a substrate 7. Both the sensor chip 6 and the substrate 7 are flat and have a substantially rectangular cross section. The long sides of the sensor chip 6 and the substrate 7 are arranged along the axis C1 and the short sides (not shown) of the sensor chip 6 and the substrate 7 are arranged perpendicular to the axis C1. The length of the short side of the substrate 7 is slightly less than the inside diameter of the tube 2 and the length of the long side of the substrate 7 is somewhat greater than the inside diameter of the tube 2. The sensor chip 6 divides the retaining chamber 5 into two chambers.

The sensor chip 6 has a thin-wall portion 6c defined at its center. A plurality of distortion gauges 17 are formed on the upper surface of the thin-wall portion 6c, namely, on pressure sensitive surface 6a. Therefore, in the embodiment of FIG. 1, the pressure sensitive surface 6a faces a direction perpendicular to the axis C1. A pad (not shown) is provided on the upper surface of the sensor chip 6 and the upper surface of the substrate 7. The pads of the sensor chip 6 and the substrate 7 are joined to each other by a bonding wire 11. Further, a lead wire of a signal cable 12 is joined to the pad of the substrate 7. The signal cable 12 passes through a through-hole 13 of the partition 4 and extends through the tube 2 reaching the basal end of the catheter.

Furthermore, the space between the inner wall of the tube 2 and the substrate 7 in the chip storage chamber 5 is filled with a silicon gel 14 that functions as a gel or liquid pressure transmitting medium.

The catheter 1 of this embodiment is inserted into a blood vessel from the cap 15 at its distal end. Therefore, the pressure inside the blood vessel initially acts on the outer surface of the cap 15 or, in other words, a force receiving surface 15a. For the material of the cap 15, biocompatible resin material such as polytetrafluoroethylene (PTFE) or vinyl chloride is used.

In the catheter 1, a pressure introducing hole 8 is formed in the peripheral portion of the sensor portion 3 in the catheter tube 2. The pressure introducing hole 8 is sealed with a seal 9 made of biocompatible silicon rubber. A space 10 is defined in a part of the substrate 7 that corresponds to the pressure introducing hole 8. The space 10 between the sensor chip 6 and the seal 9 is filled with a pressure transmitting medium. The pressure transmitting medium filling the space 10 is the silicon gel 14, which is the same as the pressure transmitting medium filling the chip retaining chamber 5. Pressure transmitting media other than the silicon gel 14 may be employed to fill the space 10, however, it is preferable that a biocompatible material be used.

The sensing operation by the blood vessel catheter 1 provided with the sensor 3 will now be described.

When there is an obstruction or a constricting portion such as a blood clot or a tumor inside a blood vessel, in which the tube 2 is inserted, the insertion resistance against the tube 2 increases when the distal end of the sensor 3, namely, the force receiving surface 15a of the cap 15, is pressed against the obstruction or the constricting portion. This increases the force acting on the force receiving surface 15a of the cap 15, which finely moves the cap 15 toward the sensor chip 6.

As a result, pressure is applied to the silicon gel 14 inside the chip retaining chamber 5, which increases the pressure applied to the pressure sensitive surface 6a. In other words, force fluctuations occurring outside the sensor 3 are indirectly transmitted to the pressure sensitive surface 6a through the silicon gel 14.

This increases distortions of the pressure sensitive surface 6a and generates variations in the electrical resistance value of the distortion gauges 17. Therefore, the sensor chip 6 outputs a signal in response to variations in the resistance value of the distortion gauges 17, that is, an analog signal S is outputted externally in response to variations in the forces applied to the catheter. The signal is inputted to an electric circuit provided at the basal end of the tube 2 via the bonding wires 11. The electric circuit process and displays the inputted signal.

Figure 2A:
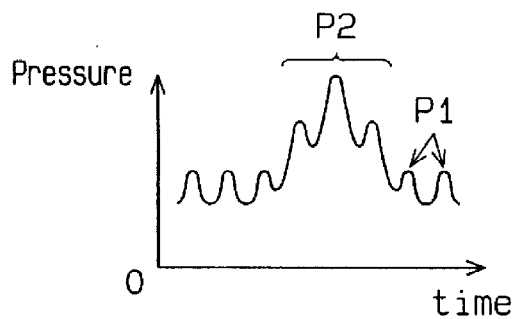
FIG. 2(a) is a graph showing a theoretical gel pressure variation waveform resulting from forces acting on the seal 9.

Detected signals will be explained with reference to FIGS. 2(a), 2(b) and 2(c).

Figure 2C:
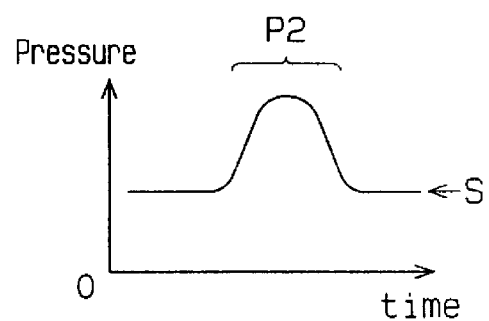
FIG. 2(c) is a graph showing the waveform of a sensor output signal.

FIG. 2(c) shows the waveform of a signal S, which is actually issued from the pressure sensor chip 6. On the other hand, the FIGS. 2(a) and 2(b) show virtual waveforms that are not actually issued. FIG. 2(a) shows the waveform representing the fluctuations of the pressure acting on the pressure sensing surface 6a of the pressure sensor chip 6, while FIG. 2(b) shows the waveform representing the fluctuations of the pressure acting on the backside 6b of the sensor chip 6.

Figure 2B:
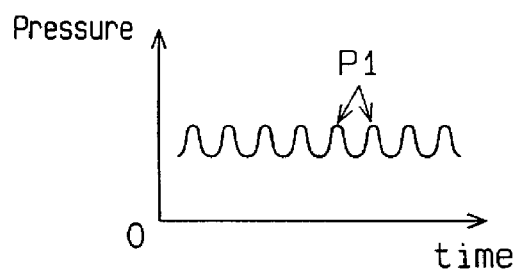
FIG. 2(b) is a graph showing a gel theoretical pressure variation waveform resulting from forces acting on the cap 15.

The graphs of FIGS. 2(b) and 2(c) include the pressure fluctuations caused by blood pressure. This fluctuation is illustrated by a plurality of identical pulses P1 in the two graphs. Each pulse P1 corresponds to one heart beat (that is, pulsating changes in the blood pressure). A pressure variation caused by a contact with an obstruction is included in the graph of FIG. 2(a) but is not included in the graph of FIG. 2(b). This pressure component is represented by a pulse P2 that is irregular and larger than the pulses P1.

When there is an obstruction in the forward travel direction of the tube 2, the cap 15 contacts the obstruction. The periphery of the tube 2, however, does not contact the obstruction. Therefore, the force caused by the contact with the obstruction does not act on the seal 9 that constitutes a part of the tube's periphery. On the other hand, since blood also exists around the periphery of the catheter tube 2, the blood pressure fluctuations positively act on the seal 9.

The thin wall 6c of the pressure sensor chip 6 receives pressures from opposite sides. The sensor chip 6 is distorted by the pressures. The pulsating component of the blood pressure acts on both sides of the thin wall 6c. The pulse P1 elements, which are not the subject of the sensing operation, cancel each other out and, as a result, are not detected. Therefore, only the sensor output signal S corresponding to the pressure fluctuation component caused by the contact with the obstruction, that is, the desired pressure fluctuation element, is obtained.

As described above, this invention produces only the desired output signal S. Referring to the data, the operator thus may correctly judge the condition in the forward travel direction such as the existence of obstructions or narrowed passages. According to the sensing result, the operator manipulates the wires to direct the distal end of the sensor 3 toward a direction in which the pressure decreases. In this manner, the operator positively guides the distal end of the catheter tube 2 to a predetermined point in the blood vessel.

An extremely small semiconductor pressure sensor chip 6 is used in the catheter 1 of FIG. 1. This makes the size of the sensor 3 compact compared to that of other apparatuses for detecting pressure and thus more useful.

The catheter 1 is characterized by that the pressure introducing hole 8 being formed in the peripheral portion of the catheter tube 2. The structure, compared to a structure in which the pressure introducing hole 8 is formed at the distal end of the catheter tube 2, has the following advantages. Forming a hole in the peripheral portion of a catheter tube 2 facilitates the attachment of the seal 9. Another advantage is that the space 10 in the substrate 7 has a simple shape. The structure does not require that catheter tube 2 be thick and therefore it serves to reduce the size of the sensor 3.

In the catheter 1, the pressure sensing surface 6a of the sensor chip 6 faces a direction perpendicular to the axis C1 of the catheter tube 2. This arrangement allows the diameter of the sensor 3 to be reduced to the length of the short sides of the sensor chip 6, and not to the length of the long sides of the sensor chip 6. Therefore, compared to a case in which the pressure sensing surface 6a faces the direction of the axis C1, the size of the sensor 3 is reduced and an increase in the diameter of the catheter tube 2 is avoided.

In the catheter 1, the pressure introducing hole 8 is sealed with the seal 9. The backside 6b of the sensor chip 6 and the substrate 7 do not directly contact organic materials such as blood. Therefore using the catheter 1 does not contribute to thrombus and also permits the sensor 3 to be highly biocompatible. Further, the seal 9, which is exposed to the outside of the sensor 3, is made of biocompatible material such as PTFE. Similarly, the silicon gel 14, which functions as a pressure transmitting medium, is made of biocompatible material. This further improves the catheter's compatibility with organisms.

In this embodiment, the silicon gel 14 is used as a pressure transmitting medium. Accordingly, pressure fluctuations are accurately transmitted to the pressure sensing surface 6a even if the pressure receiving surface 15a and the pressure sensing surface 6a are arranged in different orientations. This improves the sensitivity of the sensor 3 compared to sensors having a non-fluid material as the pressure transmitting medium. The cap 15 and the seal 16 ensure the sealing of the silicon gel 14 in the chamber 5.

In the catheter 1, pressure fluctuations acting on the seal 9 are first transmitted to the gel 14 filling the space 10 and then are transmitted to the backside 6b of the sensor chip 6. This results in a more positive transmission of pressure fluctuations as compared to a device where the space 10 is filled only with air. Thus the sensitivity of the sensor 3 is improved.

The catheter 1 has the partition 4, which parts the interior of the tube 2. The partition 4 prevents the pressure acting on the pressure receiving surface 15a from escaping toward the proximal direction. Accordingly, the pressure acting on the pressure receiving surface 15a is not decreased and is accurately transmitted to the pressure sensing surface 6a. This improves the sensitivity of the sensor 3.

The present invention is not to be limited to the above described embodiment, but may be modified as follows.

Figure 3:
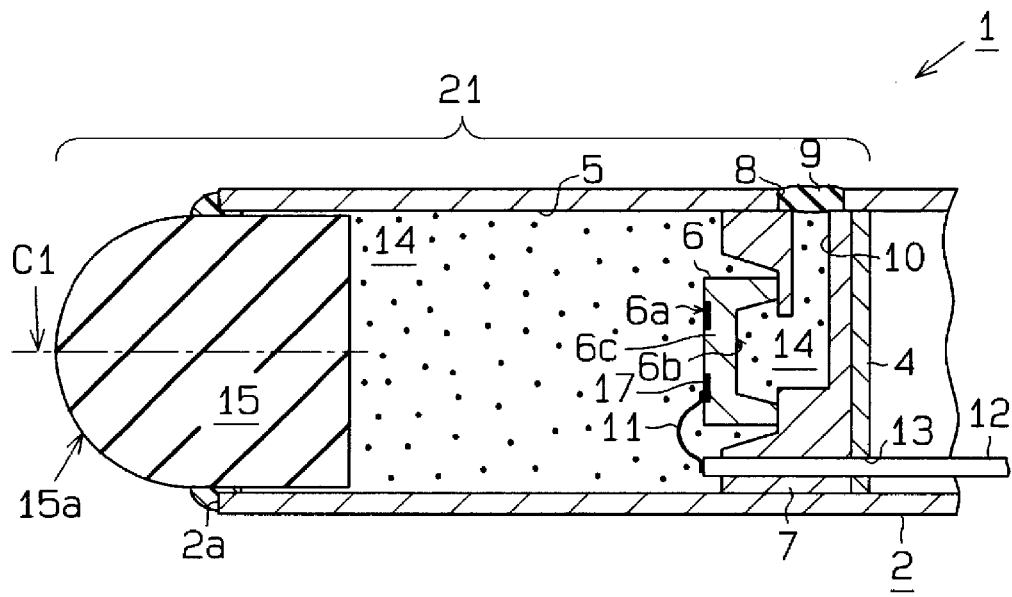
FIG. 3 is schematic cross-sectional view showing a distal portion of a catheter provided with a sensor according to a second embodiment.

FIG. 3 shows a sensor 21 of a catheter 1 according to a second embodiment. The sensor chip 6 and the substrate 7 are arranged such that the pressure sensing surface 6a is perpendicular to the axis C1. As in the first embodiment, a pressure introducing hole 8 is formed in the peripheral portion of the catheter tube 2. An L-shaped space 10 is defined in the substrate 7 at a part corresponding to the pressure introducing hole 8. The catheter 1 according to the second embodiment has the same sensing function as the first embodiment.

Figure 4:
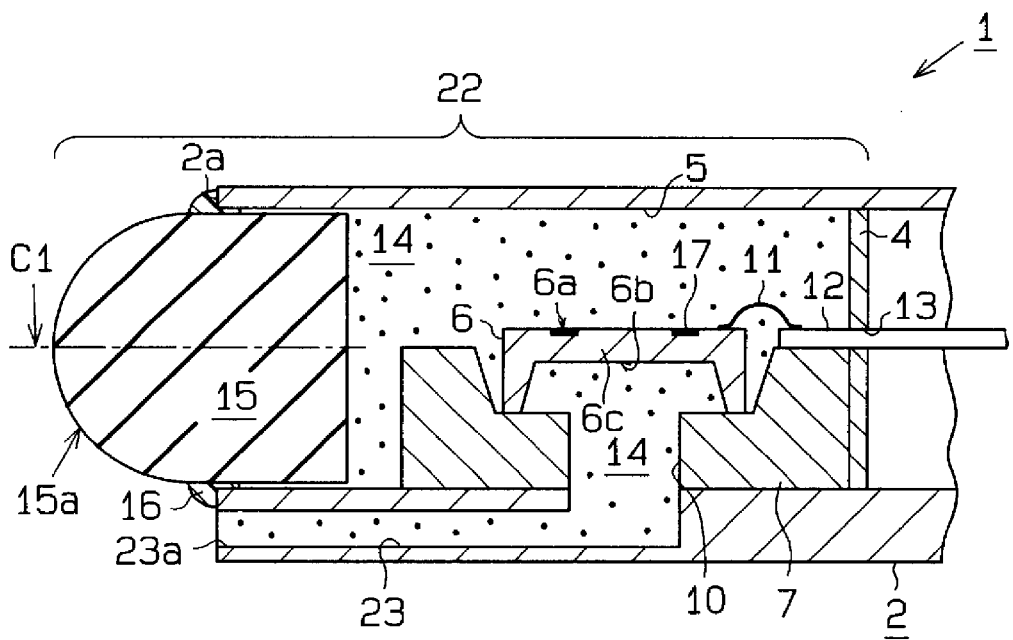
FIG. 4 is schematic cross-sectional view showing a distal portion of a catheter provided with a sensor according to a third embodiment.

FIG. 4 shows a sensor 22 of a catheter 1 according to a third embodiment. In this embodiment, a wall of the tube 2 that corresponds to the sensor 22 is formed thicker than the other parts. A passage 23 for introducing pressure is defined in the thicker part. The passage 23 opens at the distal end of the tube 2. The opening functions as a pressure introducing hole 23a in this embodiment. Since the pressure introducing hole 23a is opened to the outside, it is preferable that the silicon gel 14 in the hole 23a be substantially solidified. Therefore, according to this embodiment, the pulsation element of blood pressure is more accurately transmitted to the backside 6b of the sensor chip 6.

Figure 5:
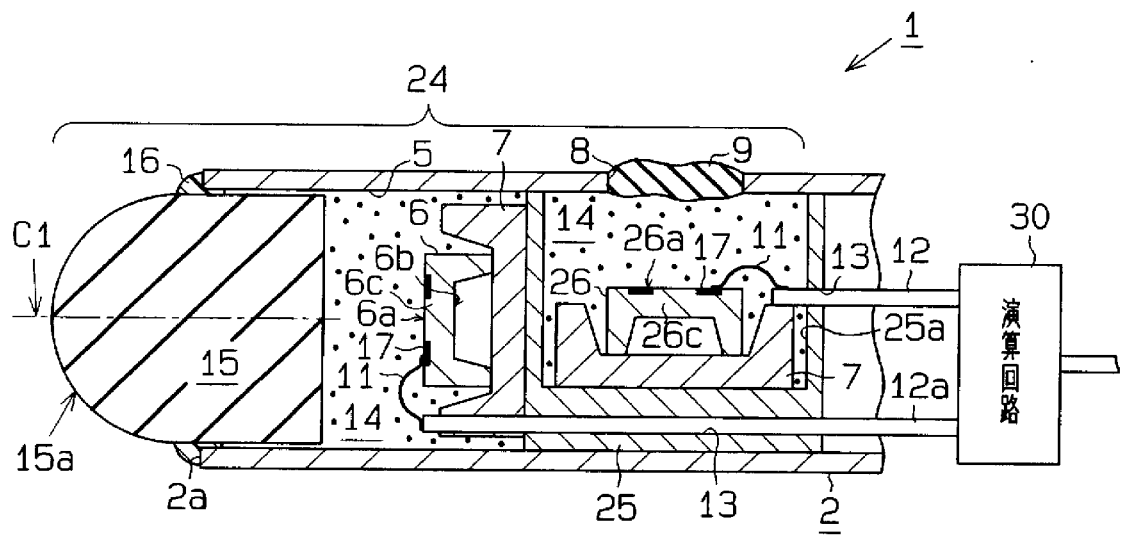
FIG. 5 is schematic cross-sectional view showing a distal portion of a catheter provided with a sensor according to a fourth embodiment.

FIG. 5 shows a sensor 24 according to a fourth embodiment. A U-shaped partition 25 is provided in the catheter tube 2. The partition 25 defines another chip retaining chamber 25a. Another substrate 7 is accommodated in the chip retaining chamber 25. A semiconductor pressure sensor chip 26 is mounted on the substrate 7. The top surface of the sensor chip 26 functions as a pressure sensing surface 26a. Silicon gel 14 fills the space about the chip 26. A pressure introducing hole 8 corresponds to the chamber 25a and is formed in the peripheral portion of the catheter tube 2. The pressure introducing hole 8 is sealed with a seal 9. Therefore, pressure fluctuations about the periphery of the tube 2 are transmitted to the pressure sensing surface 26a by the silicon gel 14. Signals (herein after referred to as adjustment signals) based on the transmitted pressure are issued externally by a signal cable 12. The adjustment signals include pressure fluctuations caused by blood pressure fluctuations. The sensor chip 6 at the distal side of the tube 2 issues sensor output signals S externally via a cable 12a. The output signals S include a component corresponding to the forces acting on the force receiving surface 15a due to contact with an object as well as a component corresponding to forces resulting from the fluctuations of blood pressure. The adjustment signals and the output signals S are inputted to an arithmetic circuit 30. The arithmetic circuit 30 eliminates the unnecessary blood pressure fluctuation waveform component from the sensor output signals S by processing the adjustment signals and the output signals S. More specifically, the arithmetic circuit 30 subtracts the adjustment signals from the output signals S. The waveform illustrated in FIG. 2(c) is thus obtained.

Figure 6:
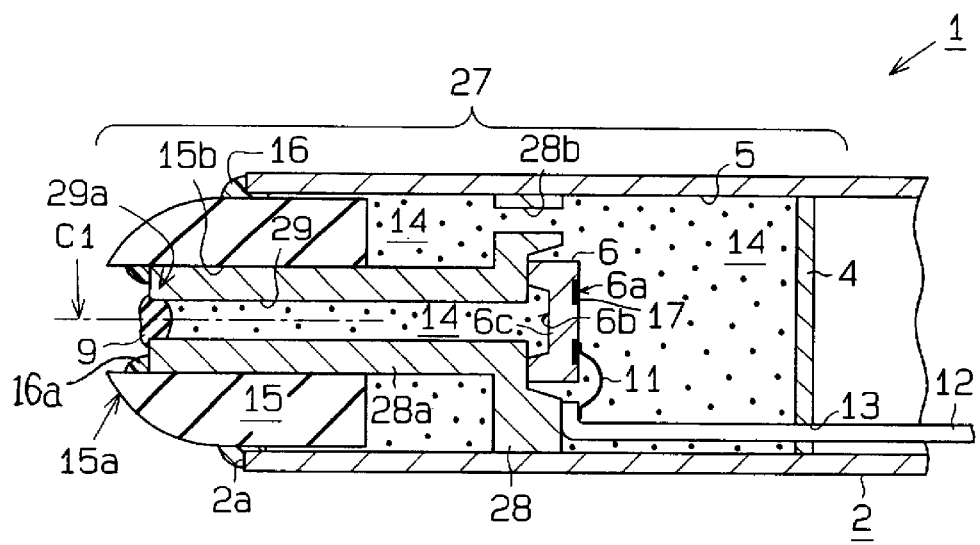
FIG. 6 is schematic cross-sectional view showing a distal portion of a catheter provided with a sensor according to a fifth embodiment.

FIG. 6 shows a sensor 27 of a catheter 1 according to a fifth embodiment. In this embodiment, a pressure sensor chip 6 and a substrate 28 are arranged on a plane perpendicular to the axis C1 such that a pressure sensing surface 6a faces toward the proximal end of the tube 2. A cylindrical sleeve 28a is formed at the center of the substrate's bottom surface 6b. A passage 29 is defined in the sleeve 28 for introducing pressure. The opening of the passage 29 functions as a pressure introducing hole 29a. The passage 29 is filled with silicon gel 14. The pressure introducing hole 29a is sealed with a seal 9. A through hole 28b is formed in the substrate 28. The through hole 28b extends parallel to the passage 29. The through hole 28b allows the silicon gel 14 to flow in the space about the sleeve 28a. A through hole 15b is formed in the center portion of the cap 15. The sleeve 28a slides with respect to the through hole 15b. A seal 16a seals the clearance between the through hole 15b and the sleeve 28a. The pressure introducing hole 29a allows the pulsation element of blood pressure to be accurately transmitted to the backside 6b of the sensor chip 6.

In the above embodiments, a gel material other than silicon gel 14 may be used as the pressure transmitting medium. Further, in some of the embodiments, a fluid material such as silicon oil may be used as the pressure transmitting medium. In consideration of its desirable characteristics, gel material such as silicon gel 14 is preferably used as the pressure transmitting medium.

In the above embodiments, the space 10 adjacent to the backside 6b of the sensor chip 6 does not need to be filled with pressure transmitting medium if pressure fluctuations are transmitted to the backside 6b. That is, the space 10 may be filled only with air. Pressure fluctuations are transmitted to the backside 6b by the air. This structure partially eliminates the necessity of adding pressure transmitting medium, thereby facilitating the manufacture of the sensors 3 and 21. In the case that the space 10 is filled with silicon rubber 14, the seal 9 may be omitted.

Therefore, the present examples and embodiments are to be considered as illustrative and not restrictive and the invention is not to be limited to the details given herein but may be modified within the scope of the appended claims.

What is claimed is:

1. A catheter having a sensor for detecting forces acting on the distal end of the catheter, the catheter comprising:
    a catheter tube;
    a chamber defined in said catheter tube;
    a sensor having first and second surfaces, accommodated in said chamber;
    a first pressure transmitting means for transmitting the forces acting on the distal end of the catheter to the first surface of the sensor;
    a second pressure transmitting means for transmitting forces acting on a peripheral portion of the catheter tube to the second surface of the sensor; and
    said sensor issuing signals in accordance with the forces transmitted to said first and second surfaces, respectively.

2. The catheter as set forth in claim 1, wherein said chamber is divided into a first and a second chamber.

3. The catheter as set forth in claim 2, wherein said sensor comprises a chip having a plate shape, said first surface comprises one side of said chip, and wherein said second surface comprises another side that is opposite to said one side.

4. The catheter as set forth in claim 3, wherein said catheter tube is hollow having an opening at the distal end and a cap for sealing said opening of said catheter tube, and wherein said first and second chambers are divided by a wall located in said catheter tube.

5. The catheter as set forth in claim 4, wherein said first pressure transmitting means comprises said cap and a pressure medium filling said first chamber, said second pressure transmitting means comprises a pressure medium filling said second chamber and a through hole formed in said catheter tube, said through hole connects the outside of said catheter tube with said second chamber, and wherein said pressure medium comprises a gel material.

6. The catheter as set forth in claim 5, further comprising a seal for sealing said through hole.

7. The catheter as set forth in claim 6, wherein said seal comprises biocompatible material.

8. The catheter as set forth in claim 1, wherein said sensor comprises a semi-conductor pressure sensor.

9. The catheter as set forth in claim 1, wherein said first surface of said sensor is parallel to the axis of said catheter tube.

10. The catheter as set forth in claim 4, wherein said cap comprises biocompatible material.

11. The catheter as set forth in claim 5, wherein said through hole is defined at a position separated from the cap toward the distal end.

12. The catheter as set forth in claim 5, wherein said pressure medium comprises gel or fluid material.

13. The catheter as set forth in claim 5, wherein said through hole is defined in said cap.

14. The catheter as set forth in claim 11, further comprising a seal for sealing said through hole.

15. A catheter having a sensor for detecting forces applied to the distal end of the catheter, the catheter comprising:
    a catheter tube;
    a chamber defined in said catheter tube;
    first and second sensors accommodated in said chamber;
    a first pressure transmitting means for transmitting the forces acting on the distal end of the catheter to said first sensor;
    a second pressure transmitting means for transmitting the forces acting on a peripheral portion of the catheter tube to said second sensor; and
    said first and second sensors issuing signals in accordance with the forces transmitted thereto, respectively.

16. The catheter as set forth in claim 15, an arithmetic means for processing two signals issued by said first and second sensor to obtain a desired signal.

17. A catheter having a distal end for insertion into a living body containing fluid, the catheter comprising:
    a catheter tube;
    a chamber defined in the catheter tube;
    a sensor means for detecting forces applied to the distal end, wherein the sensor means is located in the chamber;
    a first force transmitting means for transmitting forces applied to the tip of the distal end of the catheter to the sensor means, the forces including forces resulting from fluid pressure applied to the tip and forces resulting from contact between the tip and objects within the body;
    a second force transmitting means for transmitting forces acting on a peripheral portion of the distal end to the sensor means, wherein the peripheral portion is located such that it is not exposed to contact with objects within the body located distally of the tip of the distal end, and wherein the peripheral portion is exposed to forces resulting from fluid pressure;
    wherein the sensor means issues at least a signal representative only of contact forces applied to the tip of the distal end.

* * * * *